United States Patent
Hattori

(10) Patent No.: US 12,053,549 B2
(45) Date of Patent: Aug. 6, 2024

(54) LAXATIVE TABLET

(71) Applicant: SETOLAS Holdings, Inc., Kagawa (JP)

(72) Inventor: Atsushi Hattori, Kagawa (JP)

(73) Assignee: SETOLAS Holdings, Inc., Kagawa (JP)

(*) Notice: Subject to any disclaimer, the term of this patent is extended or adjusted under 35 U.S.C. 154(b) by 605 days.

(21) Appl. No.: 17/290,042

(22) PCT Filed: Nov. 15, 2019

(86) PCT No.: PCT/JP2019/044876
§ 371 (c)(1),
(2) Date: Apr. 29, 2021

(87) PCT Pub. No.: WO2020/101016
PCT Pub. Date: May 22, 2020

(65) Prior Publication Data
US 2021/0401754 A1    Dec. 30, 2021

(30) Foreign Application Priority Data
Nov. 16, 2018 (JP) ................. 2018-215180

(51) Int. Cl.
*A61K 9/16* (2006.01)
*A61K 9/20* (2006.01)
*A61K 33/08* (2006.01)

(52) U.S. Cl.
CPC .......... *A61K 9/2054* (2013.01); *A61K 9/2027* (2013.01); *A61K 9/2077* (2013.01); *A61K 9/2095* (2013.01); *A61K 33/08* (2013.01)

(58) Field of Classification Search
CPC . A61K 9/14; A61K 9/141; A61K 9/16; A61K 9/1605; A61K 9/1617; A61K 9/1611; A61K 9/1623; A61K 9/1629; A61K 9/1647; A61K 9/1652; A61K 9/20; A61K 9/2004; A61K 9/2009; A61K 9/2013; A61K 9/2018; A61K 9/2022; A61K 9/2027; A61K 9/2031; A61K 9/204; A61K 9/205; A61K 9/2054; A61K 9/2059
See application file for complete search history.

(56) References Cited

U.S. PATENT DOCUMENTS

| | | | |
|---|---|---|---|
| 5,169,640 A | 12/1992 | France et al. | |
| 2004/0022872 A1 | 2/2004 | Sofue et al. | |
| 2008/0305166 A1 | 12/2008 | Durig | |
| 2009/0186081 A1 | 7/2009 | Holm et al. | |
| 2012/0156293 A1* | 6/2012 | Kitajima | A61K 9/0056 424/692 |

FOREIGN PATENT DOCUMENTS

| | | |
|---|---|---|
| JP | H02-500747 A | 3/1990 |
| JP | 2003-146889 A | 5/2003 |
| JP | 2006-022060 A | 1/2006 |
| JP | 2009-522315 A | 6/2009 |
| JP | 2010-526881 A | 8/2010 |
| JP | 2010265208 A | 11/2010 |
| WO | 2011/030659 A1 | 3/2011 |

OTHER PUBLICATIONS

Kobe University, "Management of Premature Newborns," New Edition, 2000, p. 133.
Suemaru, Pharm. Health Care Sci., 29(3):337-340 (2003) (Abstract).
International Search Report mailed Feb. 18, 2020 for PCT/JP2019/044876, 7 pp.
Translation of Notice of Reasons for Refusal for Japanese Patent Application No. 2022-087199 dated May 23, 2023, 6 pages.
Xiuqiong et al., "Development and Application of New Formulations of Chinese Medicines (3rd Edition)", People Health Publishing, Jun. 1994, pp. 364-366.

* cited by examiner

*Primary Examiner* — Micah Paul Young
(74) *Attorney, Agent, or Firm* — Fox Rothschild LLP

(57) ABSTRACT

Provided is a laxative tablet which includes magnesium oxide as a main constituent, wherein (1) the particle size by volume of 50% (D50) of particles which emerge when the tablet is suspended in water is 70 μm or less as determined by laser diffractometry, (2) the particle size by volume of 90% (D90) of the particles which emerge when the tablet is suspended in water is 130 μm or less as determined by laser diffractometry, and (3) the dissolution time of the tablet when the tablet is suspended in water according to the Japanese Pharmacopoeia—general testing methods—dissolution testing methods is 10 seconds or less.

16 Claims, No Drawings

LAXATIVE TABLET

CROSS-REFERENCE TO RELATED APPLICATIONS

This application is a U.S. national phase application under 35 U.S.C. § 371 of International Patent Application No. PCT/JP2019/044876 filed Nov. 15, 2019, which claims the benefit of priority to Japanese Patent Application No. 2018-215180 filed Nov. 16, 2018, the disclosures of which are hereby incorporated by reference herein in their entireties.

TECHNICAL FIELD

The present invention relates to a laxative tablet containing magnesium oxide as a main constituent and, more specifically, to a laxative tablet which, when suspended in water, yields particles having fine particle sizes and disintegrates in a short time. The present invention also relates to a method of producing the laxative tablet.

BACKGROUND ART

Tablets containing magnesium oxide as the main ingredient have conventionally been known as antacid or laxative tablets and are still widely used. Tablets containing magnesium oxide are manufactured by combining magnesium oxide with additives such as a binders and a disintegrant, followed by tableting the mixture.

The applicant proposed antacid or laxative tablets that have high contents of magnesium oxide, disintegrate in a short time, and practically involve no tableting failure, blackening, or tableting spots (Patent Literature 1). The tablet described in Patent Literature 1 is characterized by containing 88% to 97% by weight of magnesium oxide with a specific particle size, 1% to 10% by weight of crystalline cellulose or starch as a binder, and 1% to 3.5% by weight of croscarmellose sodium or carboxystatin sodium as a disintegrant.

The applicant also proposed antacid or laxative tablets that have high contents of magnesium oxide, disintegrate quickly, maintain the characteristic of quick disintegration for a long period of time, and involve reduced occurrence of attrition and edge chipping (Patent Literature 2). The tablet described in Patent Literature 2 is characterized by containing two compounds as disintegrants in a specific ratio and having a specific shape.

Tube administration may be chosen for administering a drug to a patient with dysphagia. If a drug in the form of a tablet is to be administered via a tube, it needs to be crushed before administration. However, it has been pointed out that such dispensing of a crushed tablet may affect the physicochemical stability and efficacy of the drug after crushing, and also involve many other issues such as the complexity of the preparation work. This led to the proposal of an alternative method, in which a tablet is disintegrated and suspended in water without crushed, and the resulting dispersion is administered through a tube.

The present applicant proposed aqueous dispersion containing magnesium oxide suitable for tube administration via a feeding tube, as well as a tablet for use in preparing the same (Patent Literature 3). The tablet described in Patent Literature 3 is characterized by containing magnesium oxide having a specific particle size along with a specific binder and a specific disintegrant at predetermined ratios. This document states that the tablet disintegrates quickly in water, and the resulting aqueous dispersion can be administered smoothly without causing blockage in the feeding tube. The document also states that the feeding tube may have a diameter of about 1.0 to 6.0 mm, although one having a diameter of about 2.7 to 4.0 mm is often used for adults.

As feeding tubes for drug administration, 8Fr (outer diameter (OD): 2.7 mm) tubes are usually used for adults, while thinner tubes such as 3Fr (OD: 1.0 mm) or 4Fr (OD: 1.3 mm) are used for pediatric patients depending on their weights (Non-Patent Literatures 1 and 2). Accordingly, there has been a need for aqueous dispersion solution containing magnesium oxide that can be administered smoothly via a 3Fr feeding tube without causing blockage of dispersed particles, as well as a tablet for use in preparing the same. However, it was difficult for the aqueous suspension of magnesium oxide tablets manufactured according to the conventional formula to pass smoothly through a 3Fr feeding tube.

There has also been a demand for magnesium oxide tablets for oral administration to disintegrate quickly in the mouth in order to reduce the burden on the patient.

LIST OF CITATIONS

Patent Literature

[Patent Literature 1] JP2003-146889A
[Patent Literature 2] WO2011/030659A
[Patent Literature 3] JP2006-022060A Non-Patent Literature

[Non-Patent Literature 1] Kobe University School of Medicine, Department of Pediatrics (ed.), "Management of Premature Newborns, New Edition," Japan Pediatric Medical Publishing Co., September 2000, p. 133

[Non-Patent Literature 2] Katsuya SUEMARU and 6 others, "Drug Passability of Nasal Tubes for Children," Medical Pharmacy, Japanese Society of Pharmaceutical Health Care and Sciences, June 2003, Vol. 29, No. 3, pp. 337-340

SUMMARY OF INVENTION

Problem to be Solved by the Invention

A problem to be addressed by the present invention is to provide a laxative tablet that, when suspended in water, yields particles having fine particle sizes and disintegrates in a short time. Another problem to be addressed is to provide a laxative tablet that, when suspended in water, yields fine particles which pass through a 3Fr feeding tube smoothly, and therefore can be used for tube administration to pediatric patients.

Means to Solve the Problem

As a result of intensive research, the present inventors have succeeded in producing a laxative tablet that, when suspended in water, yields particles having fine particle sizes and disintegrates in a short time, by using specific types of disintegrants at specific ratios and employing a specific manufacturing method.

Specifically, the present invention provides the following embodiment:

[1] A laxative tablet comprising magnesium oxide as a main constituent, wherein (1) suspension of the tablet in water yields particles having a volume-based 50% particle diameter (D50) of 70 μm or less as measured by laser diffractometry,
(2) suspension of the tablet in water yields particles having a volume-based 90% particle diameter (D90) of 130 μm or less as measured by laser diffractometry, and
(3) the tablet has a disintegration time of 10 seconds or less when suspended in water according to the disintegration test method as defined in the General Tests of the Japanese Pharmacopoeia.

The laxative tablet according to the present invention may preferably be any of the following embodiments:

[2] The tablet comprising:
   0.5 to 3.5% by weight of croscarmellose sodium as Disintegrant 1; and
   0.5 to 3.5% by weight of insoluble polyvinylpyrrolidone as Disintegrant 2,
   wherein the weight ratio of the croscarmellose sodium to the insoluble polyvinylpyrrolidone is between 0.1 and 5:1.
[3] The tablet wherein the insoluble polyvinylpyrrolidone as Disintegrant 2 has a volume-based 50% particle diameter (D50) of 15 μm or less as measured by laser diffractometry.
[4] The tablet comprising 80 to 96% by weight of magnesium oxide.
[5] The tablet comprising 50 to 250 mg of magnesium oxide per tablet.
[6] The tablet for pediatric use.
[7] The tablet for use in tubal administration to a child.
[8] The laxative tablet comprising magnesium oxide as a main constituent, the tablet produced in accordance with a method comprising the steps of:
   (A1) mixing magnesium oxide having a volume-based 50% particle diameter (D50) of 0.5 to 10 μm as measured by laser diffractometry with crystalline cellulose as a binder, croscarmellose sodium as Disintegrant 1, and insoluble polyvinylpyrrolidone as Disintegrant 2, and dry granulating the mixture to produce magnesium oxide granules;
   (A2) blending the magnesium oxide granules with crystalline cellulose as a binder and a lubricant; and
   (A3) tableting the granules.
[9] The laxative tablet comprising magnesium oxide as a main constituent, the tablet produced in accordance with a method comprising the steps of:
   (B1) mixing magnesium oxide having a volume-based 50% particle diameter (D50) of 0.5 to 10 μm as measured by laser diffractometry with crystalline cellulose as a binder, and insoluble polyvinylpyrrolidone as Disintegrant 2, and dry granulating the mixture to produce magnesium oxide granules;
   (B2) blending the magnesium oxide granules with croscarmellose sodium as Disintegrant 1, crystalline cellulose as a binder, and a lubricant; and
   (B3) tableting the granules.

According to the present invention, the laxative tablet of the present invention can be prepared by Production Methods (a) and (b) mentioned below:

Production Method (A):

A method for producing a laxative tablet containing magnesium oxide as a main constituent, comprising the steps of:
   (A1) mixing magnesium oxide having a volume-based 50% particle diameter (D50) of 0.5 to 10 μm as measured by laser diffractometry with crystalline cellulose as a binder, croscarmellose sodium as Disintegrant 1, and insoluble polyvinylpyrrolidone as Disintegrant 2, and dry granulating the mixture to produce magnesium oxide granules;
   (A2) blending the magnesium oxide granules with crystalline cellulose as a binder and a lubricant; and
   (A3) tableting the granules.

Production Method (B):

A method for producing a laxative tablet containing magnesium oxide as a main constituent, comprising the steps of:
   (B1) mixing magnesium oxide having a volume-based 50% particle diameter (D50) of 0.5 to 10 μm as measured by laser diffractometry with crystalline cellulose as a binder, and insoluble polyvinylpyrrolidone as Disintegrant 2, and dry granulating the mixture to produce magnesium oxide granules;
   (B2) blending the magnesium oxide granules with croscarmellose sodium as Disintegrant 1, crystalline cellulose as a binder, and a lubricant; and
   (B3) tableting the granules.

Effect of the Invention

According to the present invention, a laxative tablet is provided that, when suspended in water, yields particles having fine particle sizes and disintegrates in a short time. When administered via a tube to patients, especially children, the tablet can be disintegrated and suspended in water, and then administered smoothly without blocking via thinner feeding tubes than those conventionally used. The tablet is also advantageous in that it has a short disintegration time in the oral cavity, reducing the burden on the patient to take them.

MODES FOR CARRYING OUT THE INVENTION

The present invention will now be explained in further details below.

<Laxative Tablet>

(Magnesium Oxide)

The volume-based 50% particle diameter (D50) magnesium oxide contained in the laxative tablet of the present invention as measured by laser diffractometry may be from 0.5 to 10 μm, preferably from 1 to 7 μm. The ratio of magnesium oxide in the tablet may be from 80 to 96% by weight, preferably from 82 to 94% by weight (accordingly, magnesium oxide is the main constituent). The content of magnesium oxide per tablet may be from 50 to 250 mg, preferably from 70 to 230 mg, more preferably from 90 to 210 mg. Examples of such magnesium oxide include Magnesium Oxide T (manufactured by Kyowa Chemical Industry).

(Disintegrant)

The laxative tablet of the present invention contains croscarmellose sodium as disintegrant 1 and insoluble polyvinylpyrrolidone as disintegrant 2. The ratio of croscarmellose sodium in the tablet may be from 0.5 to 3.5% by weight, preferably from 1 to 3% by weight. The ratio of insoluble polyvinylpyrrolidone in the tablet may be from 0.5 to 3.5% by weight, preferably from 1 to 3% by weight. The weight ratio of Disintegrant 1 to Disintegrant 2 in the tablet may be from 0.1 to 5:1, preferably from 0.3 to 4:1. The volume-based 50% particle size (D50) of insoluble polyvinylpyrrolidone as measured by laser diffractometry may be 15 μm or less, preferably 10 μm or less. Examples of insoluble polyvinylpyrrolidone having a volume-based 50% particle diameter (D50) of 15 μm or less include Kollidon CL-M (manufactured by BASF).

(Binder)

The laxative tablet of the present invention may contain a binder. Examples of binders include: crystalline cellulose, carboxyl methyl cellulose sodium, and low-substituted hydroxypropyl cellulose. Among them, crystalline cellulose may preferably be used. The ratio of the binder in the tablet may be from 3 to 15% by weight, preferably from 5 to 13% by weight.

(Lubricant)

The laxative tablet of the present invention may contain a lubricant. Examples of lubricants include: stearic acid and its salts (Na, Mg, Ca salts). Among them, calcium stearate may preferably be used. The ratio of the lubricant in the tablet may be from 0.5 to 2% by weight, preferably 0.7 to 1.5% by weight.

(Sweetener)

The laxative tablet of the present invention may contain a sweetener. Examples of sweeteners include: aspartame, acesulfame potassium, and sucralose. Among them, one or more selected from the group consisting of aspartame and Acesulfame potassium. The ratio of the sweetener in the tablet may be from 0.1 to 1% by weight, preferably 0.2 to 0.5% by weight.

(Size and Weight of the Tablet)

The diameter of the laxative tablet of the present invention may conveniently be from 5 to 12 mm, preferably from 5 to 10 mm, more preferably from 5 to 8 mm. Its thickness may conveniently be from 2 to 6 mm, preferably from 2 to 5 mm, more preferably 2.5 to 4.5 mm. Its weight per tablet may be from 50 to 300 mg, preferably from 70 to 280 mg, more preferably from 90 to 250 mg. The tablet can be made easier for children to swallow by adjusting its size and weight to within their respective ranges mentioned above.

(Disintegration Property of the Tablet)

The laxative tablet of the present invention may have a disintegration time, when suspended in water according to the disintegration test method as defined in the General Tests of the Japanese Pharmacopoeia, of 10 seconds or less, preferably 9 seconds or less, more preferably 8 seconds or less. The shorter the disintegration time, the smaller the burden on the patient to take the tablet.

(Particle Size of the Tablet after Suspended in Water)

When the laxative tablet of the present invention is suspended in water, the resulting suspended particles may have a volume-based 50% particle diameter (D50) of 70 μm or less, preferably 65 μm or less, as measured by laser diffractometry. These particles may also have a volume-based 90% particle diameter (D90) of 130 μm or less, preferably 120 μm or less, as measured by the same method.

(Volume-Based 50% Particle Diameter)

The volume-based 50% particle diameter herein refers to the particle size corresponding to 50% by volume on a cumulative distribution showing the volume fraction of particles having a certain particle size or less.

(Administration Method and Dosage)

The tablet of the present invention for laxative use may be administered orally as such or made into a disintegrated or suspended form in water and administered via tube. Its dosage may depend on the purposes or the medical conditions. The standard dosage may be 2 g per adult per day, although in the case of children, it may be administered at modified dosages depending on their ages and weights.

<Method of Producing the Laxative Tablet>

The laxative tablet of the present invention can be produced in accordance with Production Method (A) or (B) below. In other words, employing either of these methods allows for production of a tablet having the predetermined particle sizes (D50 and D90) and the predetermined disintegration time.

*Production Method (A)

A method for producing a laxative tablet containing magnesium oxide as a main constituent, comprising the steps of:
 (A1) mixing magnesium oxide having a volume-based 50% particle diameter (D50) of 0.5 to 10 μm as measured by laser diffractometry with crystalline cellulose as a binder, croscarmellose sodium as Disintegrant 1, and insoluble polyvinylpyrrolidone as Disintegrant 2, and dry granulating the mixture to produce magnesium oxide granules;
 (A2) blending the magnesium oxide granules with crystalline cellulose as a binder and a lubricant; and
 (A3) tableting the granules.

*Production Method (B)

A method for producing a laxative tablet containing magnesium oxide as a main constituent, comprising the steps of:
 (B1) mixing magnesium oxide having a volume-based 50% particle diameter (D50) of 0.5 to 10 μm as measured by laser diffractometry with crystalline cellulose as a binder, and insoluble polyvinylpyrrolidone as Disintegrant 2, and dry granulating the mixture to produce magnesium oxide granules;
 (B2) blending the magnesium oxide granules with croscarmellose sodium as Disintegrant 1, crystalline cellulose as a binder, and a lubricant; and
 (B3) tableting the granules.

The production methods mentioned above are characterized by first producing granules and then tableting the resulting granules, and also by using Disintegrant 1 and Disintegrant 2 as essential constituents. According to Production Method (A), Disintegrant 1 and Disintegrant 2 are both incorporated at the time of producing the granules. According to Production Method (B), Disintegrant 2 is incorporated at the time of producing the granules, while Disintegrant 1 is incorporated after the granules are produced. The crystalline cellulose is incorporated twice, first at the time of producing the granules and second after the production of the granules. The same type of crystalline cellulose may be used at each time, or different types of crystalline cellulose may be used.

Although either Production Method (A) or (B) may be used for producing the laxative tablet of the present invention, Production Method (A) may preferably be used from the viewpoint that the resulting tablet may have a shorter disintegration time.

Production Method (A) allows for the production of the tablet of the present invention characterized as follows.

The tablet of the present invention, which is a formulation prepared via tableting ready-for-tableting granules comprising:
 (1A) granules prepared via dry granulation of a mixture of magnesium oxide having a volume-based 50% particle diameter (D50) of 0.5 to 10 μm as measured by laser diffractometry, crystalline cellulose as a binder, croscarmellose sodium as Disintegrant 1, and insoluble polyvinylpyrrolidone as Disintegrant 2; and (2A) crystalline cellulose as a binder and a lubricant, which are present in a mixture with the granules prepared via dry granulation.

Production Method (B) allows for the production of the tablet of the present invention characterized as follows.

The tablet of the present invention, which is a formulation prepared via tableting ready-for-tableting granules comprising:

(1B) granules prepared via dry granulation of a mixture of magnesium oxide having a volume-based 50% particle diameter (D50) of 0.5 to 10 µm as measured by laser diffractometry, crystalline cellulose as a binder, and insoluble polyvinylpyrrolidone as Disintegrant 2; and (2B) croscarmellose sodium as Disintegrant 1, crystalline cellulose as a binder, and a lubricant, which are present in a mixture with the granules prepared via dry granulation.

The ready-for-tableting granules herein refer to granules that have not been tableted but are ready to be used for tableting.

The tablet obtained by Production Method (A) may contain the granules prepared by (1A) forming a core (referred to as internal excipients) and the binders of (2A) surrounding the core (referred to as external excipients). Likewise, the tablet obtained by Production Method (B) may contain the granules prepared by (1B) forming a core (referred to as internal excipients) and the binders of (2B) surrounding the core (referred to as external excipients).

EXAMPLES

The present invention will be described below in further details by reference to the following examples. However, the present invention should not be limited to these examples in any way. The properties mentioned in these examples and comparative examples were measured using the following methods.

(a) Disintegration Time

The disintegration time of each laxative tablet was measured according to the disintegration test method as defined in the General Tests of the Japanese Pharmacopoeia. Water was used as the test liquid.

(b) Volume-Based 50% Particle Diameter (D50) (Magnesium Oxide)

0.7 g of magnesium oxide was placed in a beaker with 70 mL of 0.2% sodium hexametaphosphate solution, and the mixture was subjected to dispersion treatment (3 minutes) using an ultrasonic homogenizer (Nippon Seiki, US-300). The volume-based 50% particle size (D50) of the magnesium oxide was then measured using a laser diffraction scattering particle size analyzer (Nikkiso, Microtrac).

(c) Volume-Based 50% Particle Diameter (D50) and Volume-Based 90% Particle Diameter (D90) after Suspended in Water (Laxative Tablet)

Ten tablets were placed in a beaker with 40 mL of ion-exchange water, and after left standing for 10 seconds, precipitates produced were stirred with a glass rod to make a suspension. The volume-based 50% particle size (D50) and the volume-based 90% particle size (D90) of the laxative tablets after suspended in water were then measured using a laser diffraction scattering particle size analyzer (LMS-2000e; manufactured by Seishin Kigyo).

(d) Tube Passability Test

A syringe for catheter (Enteral feeding set syringe DS20 mL, catheter yellow; manufactured by Nipro) was used. The plunger was pulled out, six tablets were placed in the barrel, and the plunger was put back. 20 mL of warm water at 55° C. was taken into the syringe from the tip of the barrel, which was then covered with a lid and left to stand naturally for 5 minutes. After 5 minutes, the syringe was subjected to 15 cycles of turning over 90 degrees and then turning back by hand, whereby the suspension was obtained. The syringe for the catheter was connected to a tube of 3Fr in thickness and 40 cm in length (Atom Nutritional Catheter T; manufactured by Atom Medical), and the suspension and 20 mL of ion exchange water for washing were injected to check the tube passage. The test was conducted three times, and the results were evaluated as OK when the tube was not blocked and NG when it was blocked.

Example 1

The laxative tablets were produced according to the formulation shown in Table 1 using the production method described below. In Tables 1 to 6, the "internal excipients" refer to the test agents used in making the granules, and the "external excipients" refer to the test agents further added to the granules once obtained. In Tables 1 to 6, the unit "mg" indicates the relative amount of each component when the amount of magnesium oxide is 100.0 mg.

Magnesium oxide with a volume-based 50% particle size (D50) of 6.5 µm: 1,500 g, crystalline cellulose: 168 g, croscarmellose sodium: 58.5 g, and insoluble polyvinylpyrrolidone 1 with a volume-based 50% particle size (D50) of 5.4 µm by laser diffractometry: 12 g were mixed, and the mixture was granulated in a roll-forming dry granulation machine at a roll pressure of 5 MPa. The granulated product was ground in an oscillator-type mill to form granules. Calcium stearate: 16 g, crystalline cellulose: 34.6 g, aspartame: 1.3 g, and acesulfame potassium: 2.7 g were added to 1540.7 g of the obtained granules and mixed in a container-type mixer to make ready-for-tableting granules. The obtained ready-for-tableting granules were tableted using a rotary tableting machine with a diameter of 6 mm and two 8R pestles at a tableting pressure of 4.5 kN to obtain magnesium oxide tablets with a weight of 120 mg per tablet, a diameter of 6 mm, and a thickness of 3.4 mm. The volume-based 50% particle size (D50), the volume-based 90% particle size (D90), the disintegration time, and the results of tube passability test of the obtained magnesium oxide tablets after suspended in water are shown in Table 7.

Example 2

The laxative tablets were produced according to the formulation shown in Table 1 using the same method used in Example 1, except that the amount of croscarmellose sodium added was changed to 52.5 g, and the amount of insoluble polyvinylpyrrolidone 1 added was changed to 18 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 7.

Example 3

The laxative tablets were produced according to the formulation shown in Table 1 using the same method used in Example 1, except that the amount of croscarmellose sodium added was changed to 43.5 g, and the amount of insoluble polyvinylpyrrolidone 1 added was changed to 27 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 7.

Example 4

The laxative tablets were produced according to the formulation shown in Table 2 using the same method used in Example 1, except that the amount of croscarmellose sodium added was changed to 35.25 g, and the amount of insoluble polyvinylpyrrolidone 1 added was changed to 35.25 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 8.

Example 5

The laxative tablets were produced according to the formulation shown in Table 2 using the same method used in Example 1, except that the amount of croscarmellose sodium added was changed to 27 g, and the amount of insoluble polyvinylpyrrolidone 1 added was changed to 43.5 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 8.

Example 6

The laxative tablets were produced according to the formulation shown in Table 2 using the same method used in Example 1, except that the amount of croscarmellose sodium added was changed to 18 g, and the amount of insoluble polyvinylpyrrolidone 1 added was changed to 52.5 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 8.

Example 7

The laxative tablets were produced according to the formulation shown in Table 3 using the same method used in Example 1, except that the amount of croscarmellose sodium added was changed to 12 g, and the amount of insoluble polyvinylpyrrolidone 1 added was changed to 58.5 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 9.

Example 8

The laxative tablets were produced according to the formulation shown in Table 3. Magnesium oxide with a volume-based 50% particle size (D50) of 6.5 μm: 1,500 g, crystalline cellulose: 168 g, and insoluble polyvinylpyrrolidone 1 with a volume-based 50% particle size (D50) of 5.4 μm by laser diffractometry: 27 g were mixed, and the mixture was granulated in a roll forming type dry granulation machine under a roll pressure of 5 MPa. The granulated product was ground in an oscillator-type mill to produce granules. To 1539.4 g of the granules obtained, 39.5 g of croscarmellose sodium, 16.3 g of calcium stearate, 35.4 g of crystalline cellulose, 1.4 g of aspartame, and 2.7 g of acesulfame potassium were added and mixed in a container-type mixer to produce ready-for-tableting granules. The obtained ready-for-tableting granules were tableted under the same conditions as in Example 1 to obtain magnesium oxide tablets with a weight of 120 mg per tablet, a diameter of 6 mm, and a thickness of 3.4 mm. The volume-based 50% particle size (D50), the volume-based 90% particle size (D90), the disintegration time, and the results of tube passability test of the obtained magnesium oxide tablets after suspended in water are shown in Table 9.

Example 9

Magnesium oxide with a volume-based 50% particle size (D50) of 6.5 μm: 3000 g, crystalline cellulose: 336 g, croscarmellose sodium: 87 g, and insoluble polyvinylpyrrolidone 1 with a volume-based 50% particle size (D50) of 5.4 μm by laser diffractometry: 54 g were mixed, and the mixture was granulated in a roll-forming dry granulation machine at a roll pressure of 5 MPa. The granulated product was ground in an oscillator-type mill to produce granules. To 3081.4 g of the obtained granules, 31.9 g of calcium stearate, 69.1 g of crystalline cellulose, 2.7 g of aspartame, and 5.3 g of acesulfame potassium were added and mixed in a container-type mixer to produce ready-for-tableting granules. The obtained ready-for-tableting granules were tableted using a rotary tableting machine with a diameter of 7.5 mm and two 11R pestles at a tableting pressure of 7 kN to obtain magnesium oxide tablets with a weight of 240 mg per tablet, a diameter of 7.5 mm, and a thickness of 4.2 mm. The volume-based 50% particle size (D50), the volume-based 90% particle size (D90), the disintegration time, and the results of tube passability test of the obtained magnesium oxide tablets after suspended in water are shown in Table 9.

Comparative Example 1

The laxative tablets were produced according to the formulation shown in Table 4 using the same method used in Example 1, except that the amount of croscarmellose sodium added was changed to 70.5 g, and insoluble polyvinylpyrrolidone 1 was not added. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 10.

Comparative Example 2

The laxative tablets were produced according to the formulation shown in Table 4 using the same method used in Example 1, except that the amount of croscarmellose sodium added was changed to 64.5 g, and the amount of insoluble polyvinylpyrrolidone 1 added was changed to 6 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 10.

Comparative Example 3

The laxative tablets were produced according to the formulation shown in Table 4 using the same method used in Example 1, except that the amount of croscarmellose sodium added was changed to 6 g, and the amount of insoluble polyvinylpyrrolidone 1 added was changed to 64.5 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 10.

Comparative Example 4

The laxative tablets were produced according to the formulation shown in Table 4 using the same method used in Example 1, except that no croscarmellose sodium was not added, and the amount of insoluble polyvinylpyrrolidone 1 was changed to 70.5 g. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 10.

Comparative Example 5

The laxative tablets were produced according to the formulation shown in Table 5 using the same method used in Example 1, except that instead of insoluble polyvinylpyrrolidone 1, insoluble polyvinylpyrrolidone 2 with a volume-based 50% particle size (D50) of 118 μm by laser diffractometry was used. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 11.

Comparative Example 6

The laxative tablets were produced according to the formulation shown in Table 5 using the same method used in Example 1, except that instead of insoluble polyvinylpyrrolidone 1, insoluble polyvinylpyrrolidone 3 with a volume-based 50% particle size (D50) of 29 μm by laser diffractometry was used. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 11.

Comparative Example 7

The laxative tablets were produced according to the formulation shown in Table 5 using the same method used in Example 1, except that instead of insoluble polyvinylpyrrolidone 1, insoluble polyvinylpyrrolidone 4 with a volume-based 50% particle size (D50) of 17 μm by laser diffractometry was used. As a result, magnesium oxide tablets with a weight of 120 mg per tablet, a diameter of 6 mm, and a thickness of 3.4 mm were manufactured. The volume-based 50% particle size (D50), the volume-based 90% particle size (D90), the disintegration time, and the results of tube passability test of the obtained magnesium oxide tablets after suspended in water are shown in Table 11.

Comparative Example 8

The laxative tablets were produced according to the formulation shown in Table 6. Magnesium oxide with a volume-based 50% particle size (D50) of 6.5 μm: 1,500 g and crystalline cellulose: 168 g were mixed and then granulated in a roll forming type dry granulation machine under a roll pressure of 5 MPa. The granulated product was ground in an oscillator-type mill to produce granules. To 1,438.5 g of the resulting granules, 37.5 g of croscarmellose sodium, 23.3 g of insoluble polyvinylpyrrolidone 1 with a volume-based 50% particle size (D50) of 5.4 μm by laser diffractometry, 15.5 g of calcium stearate, 33.6 g of crystalline cellulose, 1.3 g of aspartame, and 2.6 g of acesulfame potassium were added and mixed in a container type mixing machine to produce ready-for-tableting granules. The obtained ready-for-tableting granules were tableted under the same conditions as in Example 1 to obtain magnesium oxide tablets with a weight of 120 mg per tablet, a diameter of 6 mm, and a thickness of 3.4 mm. The volume-based 50% particle size (D50), the volume-based 90% particle size (D90), the disintegration time, and the results of tube passability test of the obtained magnesium oxide tablets after suspended in water are shown in Table 12.

Comparative Example 9

The laxative tablets were produced according to the formulation shown in Table 6. Magnesium oxide with a volume-based 50% particle size (D50) of 6.5 μm: 1,500 g, crystalline cellulose: 168 g, and croscarmellose sodium: 43.5 g were mixed and then granulated in a roll-forming dry granulation machine under a roll pressure of 5 MPa. The granulated product was ground in an oscillator-type mill to produce granules. To 1573 g of the resulting granules, 24.8 g of insoluble polyvinylpyrrolidone 1 with a volume-based 50% particle size (D50) of 5.4 μm by laser diffractometry, 16.5 g of calcium stearate, 35.8 g of crystal cellulose, 1.4 g of aspartame, and 2.8 g of acesulfame potassium were added and mixed in a container type mixing machine to produce ready-for-tableting granules. The obtained ready-for-tableting granules were tableted under the same conditions as in Example 1 to obtain magnesium oxide tablets with a weight of 120 mg per tablet, a diameter of 6 mm, and a thickness of 3.4 mm. The volume-based 50% particle size (D50), the volume-based 90% particle size (D90), the disintegration time, and the results of tube passability test of the obtained magnesium oxide tablets after suspended in water are shown in Table 12.

Comparative Example 10

The laxative tablets were produced according to the formulation shown in Table 6. Magnesium oxide with a volume-based 50% particle size (D50) of 6.5 μm: 1,500 g, crystalline cellulose: 103.5 g, croscarmellose sodium: 49.5 g, and corn starch: 33 g were mixed and then granulated in a roll-forming dry granulation machine at a roll pressure of 5 MPa. The granulated product was ground in an oscillator-type mill to produce granules. To 1543.2 g of the resulting granules, 17 g of calcium stearate was added and mixed in a container type mixing machine to produce ready-for-tableting granules. The obtained ready-for-tableting granules were tableted under the same conditions as in Example 1 to obtain magnesium oxide tablets with a weight of 113.6 mg per tablet, a diameter of 6 mm, and a thickness of 3.4 mm. The volume-based 50% particle size (D50), the volume-based 90% particle size (D90), the disintegration time, and the results of tube passability test of the obtained magnesium oxide tablets after suspended in water are shown in Table 12. The proportions of test agents in the formulation of Comparative Example 10 are based on the proportions of test agents in Example 1 and Preparation Example 1 of Patent Literature 3.

TABLE 1

|  | Test agents | Example 1 (mg) | Example 1 (%) | Example 2 (mg) | Example 2 (%) | Example 3 (mg) | Example 3 (%) |
|---|---|---|---|---|---|---|---|
| Internal excipients | Magnesium oxide | 100.0 | 83.33 | ← | | ← | |
| | Crystalline cellulose | 11.2 | 9.33 | ← | | ← | |
| | Croscarmellose sodium | 3.9 | 3.25 | 3.5 | 2.92 | 2.9 | 2.42 |
| | Insoluble polyvinyl pyrrolidone 1 | 0.8 | 0.67 | 1.2 | 1.00 | 1.8 | 1.50 |
| External excipients | Crystalline cellulose | 2.6 | 2.17 | ← | | ← | |
| | Aspartame | 0.1 | 0.08 | ← | | ← | |
| | Acesulfame potassium | 0.2 | 0.17 | ← | | ← | |
| | Calcium stearate | 1.2 | 1.00 | ← | | ← | |
| | Total | 120.0 | 100.00 | ← | | ← | |
| | Croscarmellose sodium:Insoluble polyvinylpyrrolidone | 4.88:1 | | 2.92:1 | | 1.61:1 | |

TABLE 2

|  | Test agents | Example 4 (mg) | Example 4 (%) | Example 5 (mg) | Example 5 (%) | Example 6 (mg) | Example 6 (%) |
|---|---|---|---|---|---|---|---|
| Internal excipients | Magnesium oxide | 100.0 | 83.33 | ← | | ← | |
| | Crystalline cellulose | 11.2 | 9.33 | ← | | ← | |
| | Croscarmellose sodium | 2.35 | 1.96 | 1.8 | 1.50 | 1.2 | 1.00 |
| | Insoluble polyvinyl pyrrolidone 1 | 2.35 | 1.96 | 2.9 | 2.42 | 3.5 | 2.92 |
| External excipients | Crystalline cellulose | 2.6 | 2.17 | ← | | ← | |
| | Aspartame | 0.1 | 0.08 | ← | | ← | |
| | Acesulfame potassium | 0.2 | 0.17 | ← | | ← | |
| | Calcium stearate | 1.2 | 1.00 | ← | | ← | |
| | Total | 120.0 | 100.00 | ← | | ← | |
| | Croscarmellose sodium:Insoluble polyvinylpyrrolidone | 1:1 | | 0.62:1 | | 0.34:1 | |

TABLE 3

|  | Test agents | Example 7 (mg) | Example 7 (%) | Example 8 (mg) | Example 8 (%) | Example 9 (mg) | Example 9 (%) |
|---|---|---|---|---|---|---|---|
| Internal excipients | Magnesium oxide | 100.0 | 83.33 | ← | | 200.0 | 83.33 |
| | Crystalline cellulose | 11.2 | 9.33 | ← | | 22.4 | 9.33 |
| | Croscarmellose sodium | 0.8 | 0.67 | | | 5.8 | 2.42 |
| | Insoluble polyvinyl pyrrolidone 1 | 3.9 | 3.25 | 1.8 | 1.50 | 3.6 | 1.50 |

TABLE 3-continued

|  |  | Example 7 | | Example 8 | | Example 9 | |
|---|---|---|---|---|---|---|---|
| | Test agents | (mg) | (%) | (mg) | (%) | (mg) | (%) |
| External excipients | Croscarmellose sodium | | | 2.9 | 2.42 | | |
| | Crystalline cellulose | 2.6 | 2.17 | ← | | 5.2 | 2.17 |
| | Aspartame | 0.1 | 0.08 | ← | | 0.2 | 0.08 |
| | Acesulfame potassium | 0.2 | 0.17 | ← | | 0.4 | 0.17 |
| | Calcium stearate | 1.2 | 1.00 | ← | | 2.4 | 1.00 |
| | Total | 120.0 | 100.00 | ← | | 240.0 | 100.00 |
| | Croscarmellose sodium:Insoluble polyvinylpyrrolidone | 0.21:1 | | 1.61:1 | | ← | |

TABLE 4

|  |  | Comparative Example 1 | | Comparative Example 2 | | Comparative Example 3 | | Comparative Example 4 | |
|---|---|---|---|---|---|---|---|---|---|
| | Test agents | (mg) | (%) | (mg) | (%) | (mg) | (%) | (mg) | (%) |
| Internal excipients | Magnesium oxide | 100.0 | 83.33 | ← | | ← | | ← | |
| | Crystalline cellulose | 11.2 | 9.33 | ← | | ← | | ← | |
| | Croscarmellose sodium | 4.7 | 3.92 | 4.3 | 3.58 | 0.4 | 0.33 | | |
| | Insoluble polyvinyl pyrrolidone 1 | | | 0.4 | 0.33 | 4.3 | 3.58 | 4.7 | 3.92 |
| External excipients | Crystalline cellulose | 2.6 | 2.17 | ← | | ← | | ← | |
| | Aspartame | 0.1 | 0.08 | ← | | ← | | ← | |
| | Acesulfame potassium | 0.2 | 0.17 | ← | | ← | | ← | |
| | Calcium stearate | 1.2 | 1.00 | ← | | ← | | ← | |
| | Total | 120.0 | 100.00 | ← | | ← | | ← | |
| | Croscarmellose sodium:Insoluble polyvinylpyrrolidone | 1:0 | | 10.75:1 | | 0.09:1 | | 0:1 | |

TABLE 5

|  |  | Comparative Example 5 | | Comparative Example 6 | | Comparative Example 7 | |
|---|---|---|---|---|---|---|---|
| | Test agents | (mg) | (%) | (mg) | (%) | (mg) | (%) |
| Internal excipients | Magnesium oxide | 100.0 | 83.33 | ← | | ← | |
| | Crystalline cellulose | 11.2 | 9.33 | ← | | ← | |
| | Croscarmellose sodium | 2.9 | 2.42 | ← | | ← | |
| | Insoluble polyvinyl pyrrolidone 2 | 1.8 | 1.50 | | | | |
| | Insoluble polyvinyl pyrrolidone 3 | | | 1.8 | 1.50 | | |
| | Insoluble polyvinyl pyrrolidone 4 | | | | | 1.8 | 1.50 |
| External excipients | Crystalline cellulose | 2.6 | 2.17 | ← | | ← | |
| | Aspartame | 0.1 | 0.08 | ← | | ← | |
| | Acesulfame potassium | 0.2 | 0.17 | ← | | ← | |
| | Calcium stearate | 1.2 | 1.00 | ← | | ← | |
| | Total | 120.0 | 100.0 | ← | | ← | |
| | Croscarmellose sodium:Insoluble polyvinylpyrrolidone | 1.61:1 | | ← | | ← | |

TABLE 6

|  |  | Comparative Example 8 | | Comparative Example 9 | | Comparative Example 10 | |
|---|---|---|---|---|---|---|---|
| Test agents | | (mg) | (%) | (mg) | (%) | (mg) | (%) |
| Internal excipients | Magnesium oxide | 100.0 | 83.33 | ← | | 100.0 | 88.0 |
| | Crystalline cellulose | 11.2 | 9.33 | ← | | 6.9 | 6.1 |
| | Croscarmellose sodium | | | 2.9 | 2.42 | 3.3 | 2.9 |
| | Corn starch | | | | | 2.2 | 1.9 |
| External excipients | Croscarmellose sodium | 2.9 | 2.42 | | | | |
| | Insoluble polyvinyl pyrrolidone 1 | 1.8 | 1.50 | ← | | | |
| | Crystalline cellulose | 2.6 | 2.17 | ← | | | |
| | Aspartame | 0.1 | 0.08 | ← | | | |
| | Acesulfame potassium | 0.2 | 0.17 | ← | | | |
| | Calcium stearate | 1.2 | 1.00 | ← | | 1.3 | 1.1 |
| Total | | 120.0 | 100.0 | ← | | 113.7 | 100.0 |
| Croscarmellose sodium:Insoluble polyvinylpyrrolidone | | 1.61:1 | | ← | | 1:0 | |

TABLE 7

| Analysis item | Example 1 | Example 2 | Example 3 |
|---|---|---|---|
| Suspended particle size D50 (μm) | 61.3 | 48.6 | 42.3 |
| Suspended particle size D90 (μm) | 125.7 | 105.4 | 100.9 |
| Disintegration time (seconds) | 6.5 | 6.8 | 6.8 |
| Tube passability (times) | 3/3 acceptable (OK/OK/OK) | 3/3 acceptable (OK/OK/OK) | 3/3 acceptable (OK/OK/OK) |

TABLE 8

| Analysis item | Example 4 | Example 5 | Example 6 |
|---|---|---|---|
| Suspended particle size D50 (μm) | 39.5 | 34.8 | 32.7 |
| Suspended particle size D90 (μm) | 99.6 | 97.3 | 89.3 |
| Disintegration time (seconds) | 7.6 | 7.8 | 9.0 |
| Tube passability (times) | 3/3 acceptable (OK/OK/OK) | 3/3 acceptable (OK/OK/OK) | 3/3 acceptable (OK/OK/OK) |

TABLE 9

| Analysis item | Example 7 | Example 8 | Example 9 |
|---|---|---|---|
| Suspended particle size D50 (μm) | 23.6 | 42.4 | 46.3 |
| Suspended particle size D90 (μm) | 67.3 | 97.8 | 102.9 |
| Disintegration time (seconds) | 9.8 | 7.8 | 9.0 |
| Tube passability (times) | 3/3 acceptable (OK/OK/OK) | 3/3 acceptable (OK/OK/OK) | 3/3 acceptable (OK/OK/OK) |

TABLE 10

| Analysis item | Comparative Example 1 | Comparative Example 2 | Comparative Example 3 | Comparative Example 4 |
|---|---|---|---|---|
| Suspended particle size D50 (μm) | 76.7 | 72.4 | 22.4 | 26.2 |
| Suspended particle size D90 (μm) | 150.9 | 142.7 | 64.2 | 75.4 |
| Disintegration time (seconds) | 5.0 | 5.6 | 11.3 | 13.6 |
| Tube passability (times) | 0/3 acceptable (NG/NG/NG) | 0/3 acceptable (NG/NG/NG) | 3/3 acceptable (OK/OK/OK) | 3/3 acceptable (OK/OK/OK) |

TABLE 11

| Analysis item | Comparative Example 5 | Comparative Example 6 | Comparative Example 7 |
|---|---|---|---|
| Suspended particle size D50 (μm) | 79.0 | 73.9 | 64.4 |
| Suspended particle size D90 (μm) | 155.7 | 147.3 | 131.2 |
| Disintegration time (seconds) | 5.8 | 4.6 | 6.0 |
| Tube passability (times) | 0/3 acceptable (NG/NG/NG) | 2/3 acceptable (NG/OK/OK) | 0/3 acceptable (NG/NG/NG) |

TABLE 12

| Analysis item | Comparative Example 8 | Comparative Example 9 | Comparative Example 10 |
|---|---|---|---|
| Suspended particle size D50 (μm) | 72.7 | 73.3 | 83.8 |
| Suspended particle size D90 (μm) | 157.4 | 153.4 | 161.9 |
| Disintegration time (seconds) | 6.0 | 6.3 | 6.0 |
| Tube passability (times) | 0/3 acceptable (NG/NG/NG) | 0/3 acceptable (NG/NG/NG) | 0/3 acceptable (NG/NG/NG) |

It can be understood from Tables 1 to 12 above that the laxative tablets of the present invention produce, in the state of suspension, particles with particle sizes D50 of less than 70 μm and particle sizes D90 of less than 130 μm, disintegrate within a time of less than 10 seconds, and cause no blockage in the 3Fr tube passability test.

INDUSTRIAL APPLICABILITY

The laxative tablet of the present invention produces particles with fine particle sizes when suspended in water and disintegrates in a short time. When administered to patients, especially children, via tube, the tablet can be disintegrated and suspended in water, and administered smoothly without causing blockage of a feeding tube thinner than the conventional feeding tube. The tablet has a short disintegration time also in the oral cavity, thereby reducing the burden on the patient to take it.

The invention claimed is:

1. A laxative tablet comprising magnesium oxide as a main constituent, wherein the tablet is made by a process comprising the steps of:
   (1) mixing magnesium oxide with internal excipients to form a mixture, wherein the internal excipients include a first disintegrant comprising insoluble polyvinylpyrrolidone, and a binder; and dry granulating the mixture to produce magnesium oxide granules;
   (2) blending the magnesium oxide granules with one or more external excipients to produce blended granules; and
   (3) tableting the blended granules;
   wherein suspension of the tablet in water yields particles having a volume-based 50% particle diameter (D50) of 70 μm or less as measured by laser diffractometry,
   suspension of the tablet in water yields particles having a volume-based 90% particle diameter (D90) of 130 μm or less as measured by laser diffractometry, and
   the tablet has a disintegration time of 10 seconds or less when suspended in water according to the disintegration test method as defined in the General Tests of the Japanese Pharmacopoeia.

2. The tablet according to claim 1, wherein the tablet further comprises a second disintegrant, wherein:
   the first disintegrant comprises 0.5 to 3.5% by weight of insoluble polyvinylpyrrolidone, and
   the second disintegrant comprises 0.5 to 3.5% by weight of croscarmellose sodium;
   wherein the weight ratio of the croscarmellose sodium to the insoluble polyvinylpyrrolidone is in the range of 0.1:1 to 5:1.

3. The tablet according to claim 1, wherein the insoluble polyvinylpyrrolidone has a volume-based 50% particle diameter (D50) of 15 μm or less as measured by laser diffractometry.

4. The tablet according to claim 1, comprising 80 to 96% by weight of magnesium oxide.

5. The tablet according to claim 1, comprising 50 to 250 mg of magnesium oxide per tablet.

6. The tablet according to claim 1 for pediatric use.

7. The tablet according to claim 1 for use in tubal administration to a child.

8. A method for producing a laxative tablet containing magnesium oxide as a main constituent, comprising the steps of:
   (1) mixing magnesium oxide with internal excipients to form a mixture, wherein the internal excipients include a first disintegrant comprising insoluble polyvinylpyrrolidone, and a binder; and dry granulating the mixture to produce magnesium oxide granules;
   (2) blending the magnesium oxide granules with one or more external excipients to produce blended granules; and
   (3) tableting the blended granules.

9. The method of claim 8, wherein the internal excipients further include a second disintegrant, and the one or more external excipients include a binder and a lubricant.

10. The method of claim 8, wherein the one or more external excipients include a second disintegrant, a binder, and a lubricant.

11. The method of claim 8, wherein:
    the magnesium oxide has a volume-based 50% particle diameter (D50) of 0.5 to 10 μm as measured by laser diffractometry;
    the binder comprises crystalline cellulose;
    the internal excipients further include croscarmellose sodium; and
    the external excipients include crystalline cellulose and a lubricant.

12. The method of claim 8, wherein:
    the magnesium oxide has a volume-based 50% particle diameter (D50) of 0.5 to 10 μm as measured by laser diffractometry;
    the binder comprises crystalline cellulose; and
    the external excipients include croscarmellose sodium, crystalline cellulose, and a lubricant.

13. The tablet according to claim 1, wherein:
    the magnesium oxide has a volume-based 50% particle diameter (D50) of 0.5 to 10 μm as measured by laser diffractometry, the binder comprises crystalline cellulose, the internal excipients further include a second disintegrant comprising croscarmellose sodium; and
    the one or more external excipients include crystalline cellulose and a lubricant.

14. The tablet according to claim 1, wherein:
    the magnesium oxide has a volume-based 50% particle diameter (D50) of 0.5 to 10 μm as measured by laser diffractometry, the binder comprises crystalline cellulose; and
    the one or more external excipients include a second disintegrant comprising croscarmellose sodium, crystalline cellulose, and a lubricant.

15. The tablet according to claim 1, wherein the internal excipients further include a second disintegrant, and wherein the one or more external excipients include a binder and a lubricant.

16. The tablet according to claim 1, wherein the one or more external excipients include a second disintegrant, a binder and a lubricant.

* * * * *